United States Patent [19]

Janisiewicz

[11] Patent Number: 4,950,472
[45] Date of Patent: Aug. 21, 1990

[54] BIOCONTROL OF GREY-MOLD IN POME FRUITS USING *ACREMONIUM BREVE*

[75] Inventor: Wojciech J. Janisiewicz, Martinsburg, W. Va.

[73] Assignee: The United States of America as represented by the Secretary of Agriculture, Washington, D.C.

[21] Appl. No.: 159,915

[22] Filed: Feb. 24, 1988

[51] Int. Cl.$^5$ ............................................. A01N 63/00
[52] U.S. Cl. ................................. 424/93; 435/252.1; 435/252.34; 435/252.3; 435/254; 435/874; 435/926
[58] Field of Search .......... 424/93; 435/252.1, 252.34, 435/252.3, 874, 926, 254

[56] References Cited

PUBLICATIONS

A. Tronsomo et al., "The Use of Trichoderma Species to Control Strawberry Fruit Rots".
Neth. J. Pl., 83, (Supp. 1): 449–455, (1977).
P. L. Pusey et al., "Postharvest Biological Control of Stone Fruit Brown Rot by *Bacillus subtilis*", Plant Dis., 68:753–756, (1984).
A. Tronsomo et al., "Biological Control of *Botrytis cinerea* on Apple," Plant Dis., 64:1009, (1980).
C. L. Wilson et al., "Potential for Biological Control of Postharvest", Plant Dis., 69:375–378, (1985).
W. J. Janisiewicz, "Biocontrol of Two Postharvest Diseases of Apples with a Yeast," Phytopathol., 76:1133, (1986).

*Primary Examiner*—Howard E. Schain
*Attorney, Agent, or Firm*—Stephen C. Wieder; M. Howard Silverstein

[57] ABSTRACT

A process for biologically controlling the postharvest disease, grey-mold, in pome fruits using a strain of *Acremonium breve* having the identifying characteristics of NRRL 18307. The organism is isolated from apples leaves and is applied to the fruits in a aqeous suspension using conventional techniques. The organism of the invention maybe used in combination with other biocontrol agents to simultaneously control more than one postharvest disease affecting the fruit. Also disclosed is a biologically pure culture of *Acremonium breve*, NRRL 18307.

7 Claims, 3 Drawing Sheets

BIOCONTROL OF GREY-MOLD IN POME FRUITS USING *ACREMONIUM BREVE*

BACKGROUND OF THE INVENTION

1. Field of the Invention

The present invention relates to the biological control of postharvest diseases in fruits. More particularly, this invention relates to the use of *Acremonuim breve*, "*A. breve*," to biologically control the postharvest disease, grey-mold, in pome fruits.

2. Description of the Prior Art

Grey-mold, a major postharvest disease of fruit, is caused by the fungus, *Botrytis cinerea* Pers. ex Fril, "*B. cinerea*." Primarily a storage disease, grey-mold rot, as well as other fungi-induced postharvest diseases, causes considerable economical losses to the fruit industry each year.

Traditional attempts to control post-harvest diseases have involved the treatment of the fruit, after harvest and before storage, with a fungicide. However, increasing numbers of fungicide-tolerant strains of pathogens associated with postharvest diseases, as well as the need for fungicides which are safe to the environment and humans, have created the necessity for alternatives methods to control these diseases.

One alternative has been the use of biological agents to control postharvest diseases in fruit. Brown rot in peaches caused by *Monilinia fructicola* (Wint.) Honey was sucessfully controlled with *Bacillus subtilis*. Pusey et al. [Plant Dis. 86:753–756 (1984)]; Wilson et al. [Plant Dis. 69:375–378 (1985)]. *Trichoderma viride* Pers. & S. F. Gray applied to strawberry plants in the field partially controlled grey-mold on strawberry fruits after harvest. Tronsmo et al. [Neth. J. Plant Pathol. 83(suppl. 1): 449–455(1977)]. Also, partial control of rot in apples caused by *B. cinerea* flower infection was obtained by applying conidia *T. harzianium* Rifai to apple trees during bloom. Control was comparable to prior known fungicidal treatments. Tronsmo et al. [Plant Dis. 64:1009 (1980)].

SUMMARY OF THE INVENTION

I have discovered a strain of *A. breve* which is highly effective to control grey-mold rot in pome fruits. Viable cultures of the strain have been deposited with the culture collection at the North Regional Research Center, U.S. Department of Agriculture, Peoria, Illinois, 61604, under the accession number NRRL 18307. Progenies of the strain will be available during the pendency of the patent application to one determined by the Commissioner of Patents and Trademarks to be entitled thereto under 37 CFR 1.14 and 35 USC 122. All restrictions on the availability of progenies of the strain to the public will be irrevocably removed upon the granting of the patent of which the strain is the subject.

Accordingly, it is an object of the invention to provide a biological control agent which is highly effective to control grey-mold in pome fruits.

It is also an object of the invention to provide a method for biologically controlling grey-mold in pome fruits, before or after harvest.

Another object of the invention is to provide a method for biologically controlling grey-mold in these fruits which eliminates the use of fungicidal treatments.

Still another object of the invention is provide a method for simultaneously controlling two or more pathogens causing post-harvest diseases in pome fruits.

In accordance with my invention, pome fruits are subjected to an aqueous suspension of strain NRRL 18307 in an amount effective to inhibit the development of the pathogen, *B. cinerea*.

DETAILED DESCRIPTION OF THE INVENTION

Figure 1:
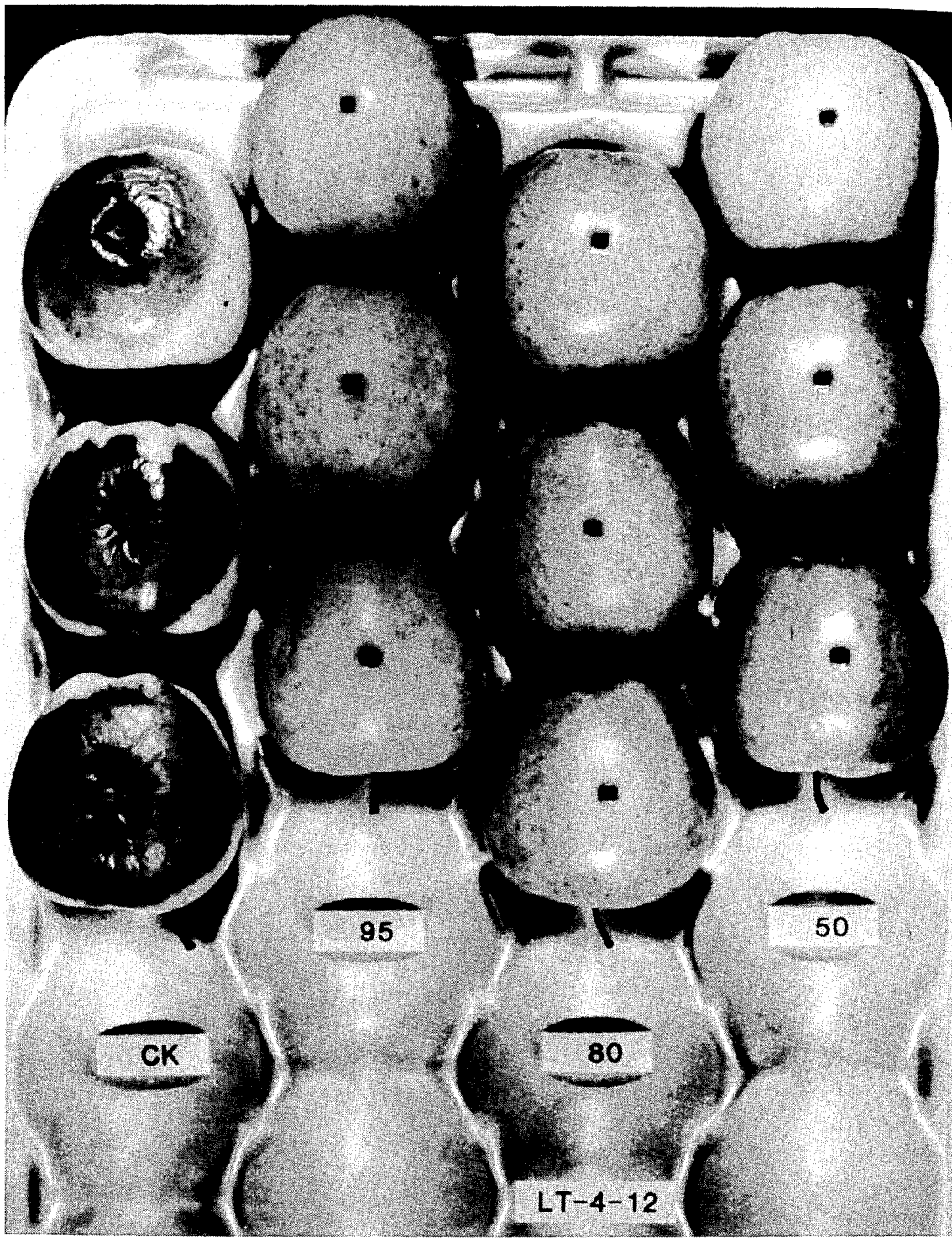
FIG. 1. The effect of antagonist (LT-4-12) on grey-mold development on 'Golden Delicious' apples. Ck-control apples inoculated with the grey-mold fungus only; 95, 80, 50 (different concentrations of the antagonist, % turbity) apples protected with the antagonist and then inoculated with the grey-mold fungus. LT-4-12=*Acremonium breve*, NRRL 18307.
Figure 2:
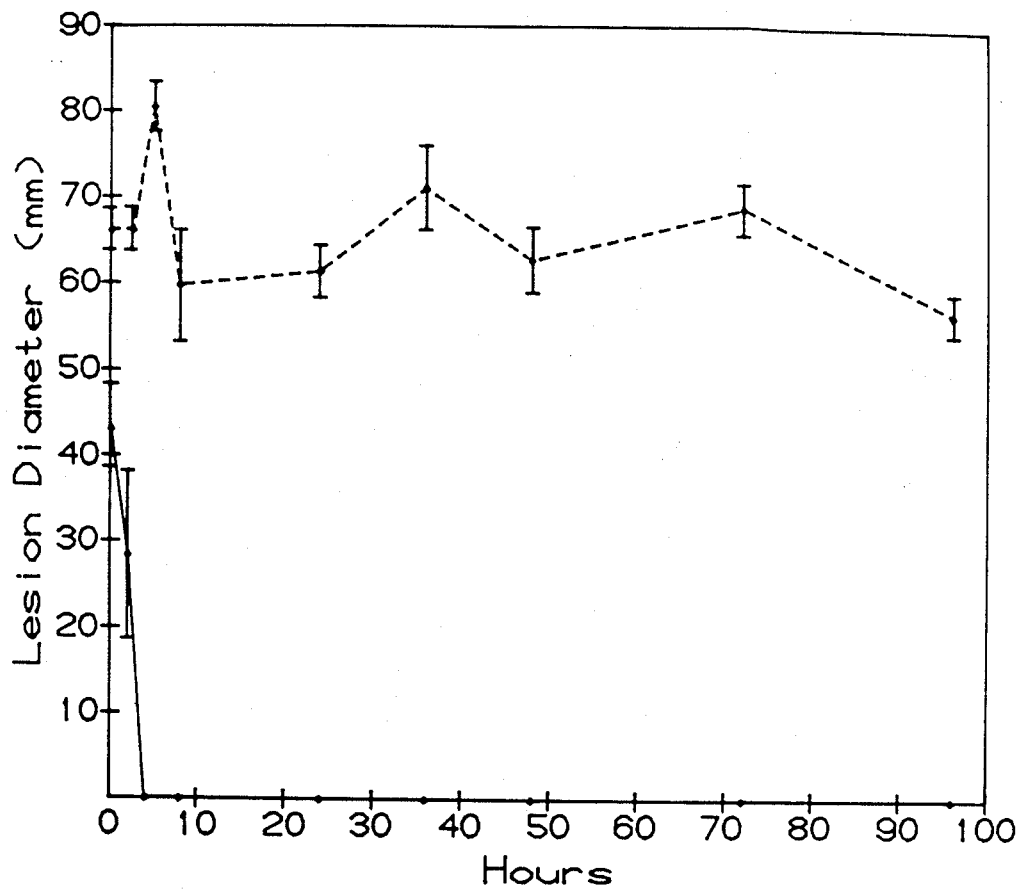
FIG. 2. Lesion development on wounded 'Golden Delicious' apples protected with *Acremonium breve*, NRRL 18307, and inoculated with *Botrytis cinerea* spores at different times following antagonist application. Antagonist treatment (———) and Control (— —).

Strain NRRL 18307 is isolated from apple leaves by repeatedly washing the leaves with a suitable aqueous buffer, i.e. a phosphate buffer and the like. Thereafter, the organisms are plated and grown on a nutritionally rich medium sufficient to support growth of the organism. For optimum growth, the preferred medium is either nutrient yeast dextrose broth (NYDB) or nutrient yeast dextrose agar (NYDA).

Strain NRRL 18307 has the following characteristic description: Colonies were 32 mm in diameter after 6 days on potato dextrose agar at 24° C., mostly moist with synnematogen especially towards the center. Colony color is dull yellow to cream under fluoresecent light, becoming orange under black light. Phialides, often indistinguishable from hypha, are unbranched, smooth, 15 to 20μ long with no collarette. Conidia are globose to obovate and are formed into heads.

Growth of strain NRRL 18307 is effected under aerobic conditions at any temperature satisfactory for growth of the organism, i.e. from about 4° C. to about 28° C.; the preferred temperature range is about 22° C. to 26° C. The pH of the nutrient media is about pH 6.5 to 6.9. The incubation time is that time necessary for the organism to reach a stationary phase of growth, preferably, from about 40 to 60 hours.

Strain NRRL 18307 may be grown in any conventional shake flask for small fermentation runs. For larger scale operations, it is convenient to carry out the culture in a fermentation tank, while applying agitation and areation to the inoculated liquid medium. Following incubation, the organism is harvested by conventional sedimentary methodology, i.e. centrifugation or filtering. The resulting pellets are stored until use.

For the purpose of the invention, the term "pome fruit" is used herein to designate fruits having a fleshy outer layer and a central core with seeds enclosed in a capsule. Suitable pome fruits include, but are not limited to, apple, pears and the like.

In accordance with the invention, strain NRRL 18307 is applied to the fruits in suspension with water. The suspension may optionally contain conventional additives such as surfactants and antioxidants. Aqueous suspensions of strain NRRL 18307 may be applied to the fruit using any conventional techniques, such as spraying, dipping or brushing. The treatments may be applied to the fruits before or after harvest. Preferably, the treatments are applied after harvest and prior to storage.

Concentrations of aqueous suspensions of strain NRRL 18307 useful in the process of the invention are any concentrations which inhibits the development of B. cinerea when applied to pome fruits. As will be obvious to the skilled artisan, effective concentrations will vary depending upon such factors as the ripeness of the fruits and the concentration of the pathogen affecting the fruit. Exemplary concentrations range from about $2.5 \times 10^5$ cells/ml to about $9.5 \times 10^6$ cell/ml; the most preferred concentration ranges from $3.4 \times 10^6$ to $9.5 \times 10^6$ cells/ml.

It is within the compass of the invention to treat the fruits with strain NRRL 18307 alone or in combination with other biological control agents which are effective to control other pathogens inciting postharvest diseases in pome fruit. When used, these agents should be used in amount, as readily determined by one skilled in the arts, which will not interfere with the effectiveness of organism of the invention.

The following examples are intended to further illustrate the invention and not to limit the scope of the invention as defined by the claims.

EXAMPLE I

The effectiveness of strain NRRL 18307 to inhibit the development of B. cinerea spores in wounded Golden Delicious apples was demonstrated.

Strain NRRL 18307 was isolated using the following procedure: Leaves were picked throughout the 1985 growing season from Golden Delicious apples trees in 4 blocks of 5 trees in each block, scattered over approximately a 4 acre area. 10 leaves were collected from different parts of trees in each block. The samples were washed in phosphate buffer by shaking in a beaker on a rotary shaker for 10 minutes at 100 rpm. The buffer from the first washing was discarded and the leaves were washed a second time with 30 seconds of sonication in a Bransonic 521 sonicator at the beginning of the wash. The washing was plated on NYDA medium and incubated for 48 hours. Appearing colonies were isolated and purified using standard purification techniques.

Strain NRRL 18307 was grown in NYDB liquid medium for 48 hours on a shaker at 150 rpm. The culture was centrifuged at 7000 rpm for 10 minutes and the resulting pellet was suspended in water at various concentrations. Concentrations of the aqueous suspensions were adjusted on spectrophotometer.

Apples wounds 3 mm deep and 3 mm wide were inoculated with 20 $\mu$l of an aqueous suspension of strain NRRL 18307 having a concentration of $2.5 \times 10^5$ cells/ml, $3.4 \times 10^6$ cells/ml or $9.5 \times 10^6$ cells/ml. Shortly thereafter, the wounds were inoculated with 20 $\mu$l of $1 \times 10^4$ spore/ml of an aqueous suspension of B. cinerea spores. Control apples were inoculated with 20 $\mu$l of the aqueous suspension of B. cinerea spores only.

Lesion diameter was measured after 7 days incubation at 24° C. Each apple constituted a single replicate and each treatment was replicated 3 times.

At each concentration tested, Strain NRRL 18307 inhibited the development of the pathogen, B. cinerea. As shown in FIG. 1, total protection occurred on all treated apples. Further, protection was ongoing for a prolonged period of time. After the apples were left standing for 10 week, no new lesions developed.

EXAMPLE II

The ability of strain NRRL 18307 to inihibit B. cinerea spore germination in vitro was demonstrated. The abbreviation "CFU" is used herein to designate colony forming units.

An aqueous suspension of strain NRRL 18307 was prepared as described in Example I at a concentration of $9.5 \times 10^6$ CFU/ml. In 16 mm diameter wells of plastic tissue culture plates, three 100 $\mu$l portions of an aqueous suspension of strain NRRL 18307 was mixed respectively with 100 $\mu$l of an aqueous suspension containing either $1 \times 10^3$ spores/ml, $1 \times 10^4$ spores/ml or $1 \times 10^5$ spores/ml of the pathogen, B. cinerea.

The plates were incubated at 24° C. The plates were first examined at 72 hours of incubation and at this point, equal volumes of freshly squeezed apple juice were added to the plates. After an additional 48 hrs of incubation (120 hrs from the beginning of the experiment), the plates were examined a second time. Each well constituted a single replicate and each treatment was replicated three times. Germination was determined according to arbitrary scales by examination under an inverted microscope.

Results were analyzed and are recorded in Table I.

As shown in Table I, strain NRRL 18307 strongly inhibited spore germination in vitro after 72 hours. The addition of apple juice did not increase germination. Thus, while the mode of action of strain NRRL 18307 to inhibit B. cinerea is not known, these results suggest that strain NRRL 18307 may, at least partially, operate to inhibit spore germination of B. cinerea in the fruit.

EXAMPLE IV

Combination treatments containing various concentrations of A. breve, strain NRRL 18307, and Pseudomanas sp. were tested on Golden Delicious apples using spore mixtures of B. cinerea and Penicillium expansum, "P. expansum", the pathogen which causes the postharvest disease, blue-mold. 20 $\mu$l of a water suspension containing a mixture of strain NRRL 18307 and Pseudomanas sp. was applied to apple wounds 3 mm wide and 3 mm deep. Within about 15 minutes, 20 $\mu$l of an aqueous suspension of B. cinerea/P. expansum spore mixture were added to the wounds. The spore mixtures consisted of a constant concentration of $1 \times 10^4$ B. cinerea spores/ml and a concentration from 0 to $1 \times 10^7$ in ten-fold increases of P. expansum spores. Concentrations of mixtures of strain NRRL 18307 and Pseudomanas sp. in the aqueous suspensions varied as shown in Table II.

Lesions diameter was measured 7 days after inoculation at 24° C. Each apple consisted of a single replicate and each treatment was replicated 3 times. The results were as presented in FIG. 3.

Figure 3:
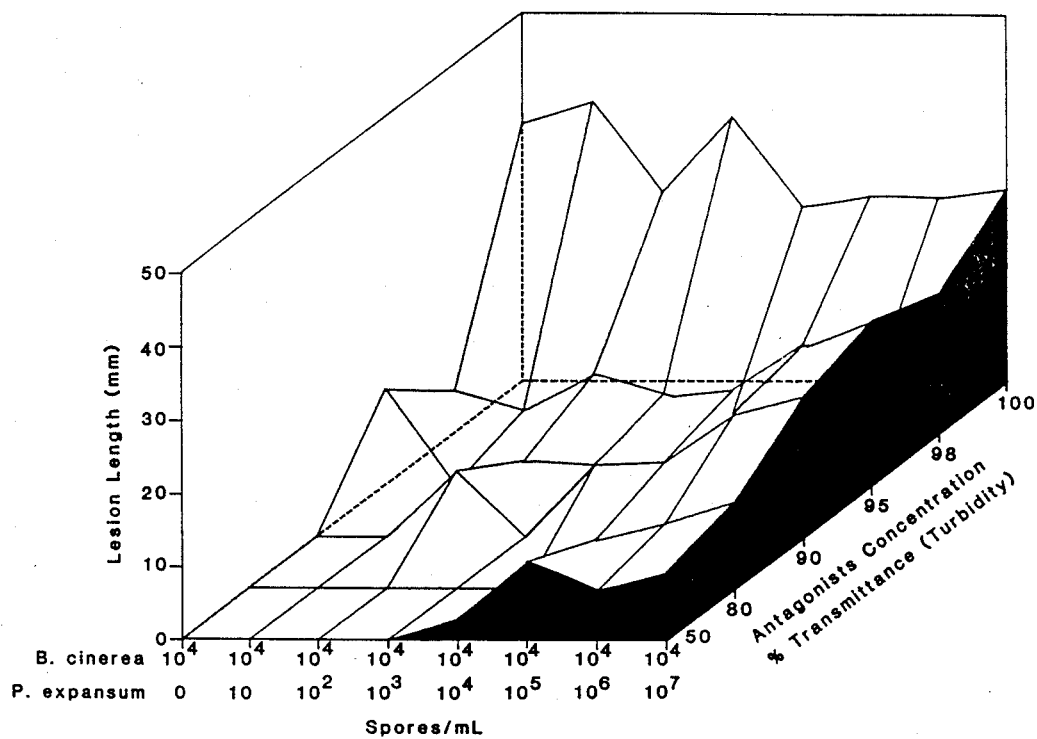
FIG. 3. The effect of antagonist mixture of *A. breve* strain NRRL 18307 and Pseudomonas sp. on lesion development resulting from inoculation of wounded 'Golden Delicious' apples with *B. cinerea* and *P. expansum* spore mixtures.

Both pathogens, P. expansum and B. cinerea, were effectively controlled simultaneously when the apples were inoculated with mixture containing A. breve, NRRL 18307, and Pseudomanas sp. There was a strong tendency toward reduction in lesion size in all spore mixtures as concentrations of the control agents increased. As shown in FIG. 3, the two highest concentrations of NRRL 18307/Pseudomonas sp. mixtures prevented lesion development on fruit inoculated with spore mixtures containing from 0 to $1 \times 10^3$ spores/ml of *P. expansum*. This was also true for the third highest concentration of antagonists mixtures, except for spore mixtures containing *P. expansum* at $1 \times 10^2$ spores/ml where small lesions occurred. Also, no lesions developed at concentrations of 95% and 80% Transmitance with $1 \times 10$ and $1 \times 10^4$ spores/ml of *P. expansum*, respectively, in the mixtures.

Advantageously, strain NRRL 18307 acts very rapidly on pome fruits to control grey-mold in commerically acceptable concentrations. Further, the treatments may be used in combination with other biological agents to simultaneously control two or more pathogens causing postharvest diseases in pome fruits.

It is understood that modifications and variations maybe made to the foregoing disclosure without departing from the spirit and scope of the invention.

TABLE I

Germination of *B. cinerea* spores in vitro in water suspensions of *Acremonium breve*, strain NRRL 18307[a]

| Pathogen | Antagonist | hr | Pathogen spore concentration (spores/milliliter) | | |
|---|---|---|---|---|---|
| | | | $10^3$ | $10^4$ | $10^5$ |
| B. cinerea | NRRL 18307 | 72 | +[b] | + | + |
| | | 120 | + | + | + |
| | Control | 72 | ++ | ++ | + |
| | | 120 | +++ | +++ | +++ |

[a] at a concentration of $9.5 \times 10^6$ CFU/ml.
[b] symbols:
− = No germination;
+ = Less than ⅓ germinated;
++ = ⅓-⅔ germinated;
+++ = More than ⅔ germinated

TABLE II

Conversion of Concentrations of Aqueous Suspensions of Antagonist mixtures from % Transmittance to CFU/ml.

| % Transmittance at 420 nm | CFU/ml in mixture | |
|---|---|---|
| | Pseudomonas sp. | Acremonium breve NRRL 18307 |
| 100 | 0 | 0 |
| 98 | $8 \times 10^6$ | $1.5 \times 10^4$ |
| 95 | $9 \times 10^7$ | $2.5 \times 10^5$ |
| 90 | $1 \times 10^8$ | $1.2 \times 10^6$ |
| 80 | $3.6 \times 10^8$ | $3.4 \times 10^6$ |
| 50 | $8.5 \times 10^8$ | $9.5 \times 10^6$ |

We claim:

1. A process for biologically controlling the postharvest disease grey-mold in pome fruits comprising subjecting the fruit to an aqueous solution of a strain of *Acremonium breve* having the identifying characteristics of NRRL 18307 in an amount effective to inhibit the development of *Botrytis cinerea*.

2. The process of claim 1 wherein the concentration of the aqueous suspension is from about $2.5 \times 10^5$ cells/ml to about $9.5 \times 10^6$ cells/ml.

3. The process of claim 2 wherein the concentration of the aqueous suspension is from about $3.4 \times 10^6$ cells/ml to $9.5 \times 10^6$ cells/ml.

4. The process of claim 1 wherein the fruit is selected from the group consisting of apples and pears.

5. A process for simultaneously controlling the postharvest diseases blue-mold and grey-mold in pome fruits comprising subjecting the fruit to an effective inhibiting amount of a mixture which comprises a biological control agent effective to inhibit the development of *Botcytis cinerea*, wherein said agent is a strain of *Acremonium breve* having the identifying characteristics of NRRL 18307, and a biological control agent effective to inhibit the development of *Penicillium expansum*.

6. The process of claim 5 wherein the biological control agent effective to inhibit the development of *Pencillin expansum* is Pseudomonas sp.

7. A biologically pure culture of a strain of *Acremonium breve* having the identifying characteristic of NRRL 18307.

* * * * *